US010905452B1

(12) United States Patent
Silva et al.

(10) Patent No.: US 10,905,452 B1
(45) Date of Patent: *Feb. 2, 2021

(54) VERTEBRA PICK DEVICE

(71) Applicants: Octavio Silva, Yorba Linda, CA (US);
Fernando Silva, Westminster, CA (US)

(72) Inventors: Octavio Silva, Yorba Linda, CA (US);
Fernando Silva, Westminster, CA (US)

( * ) Notice: Subject to any disclaimer, the term of this patent is extended or adjusted under 35 U.S.C. 154(b) by 1204 days.

This patent is subject to a terminal disclaimer.

(21) Appl. No.: 14/690,439

(22) Filed: Apr. 19, 2015

(51) Int. Cl.
*A61B 17/32* (2006.01)
*A61B 17/16* (2006.01)
*A61B 1/00* (2006.01)
*A61B 1/06* (2006.01)
*A61B 1/317* (2006.01)
*A61B 1/07* (2006.01)
(Continued)

(52) U.S. Cl.
CPC .... *A61B 17/320016* (2013.01); *A61B 1/0008* (2013.01); *A61B 1/00087* (2013.01); *A61B 1/00094* (2013.01); *A61B 1/00096* (2013.01); *A61B 1/018* (2013.01); *A61B 1/0676* (2013.01); *A61B 1/07* (2013.01); *A61B 1/317* (2013.01); *A61B 17/1671* (2013.01); *A61B 17/32* (2013.01); *A61B 1/00* (2013.01); *A61B 1/00112* (2013.01); *A61B 1/00163* (2013.01); *A61B 1/00165* (2013.01); *A61B 5/0075* (2013.01); *A61B 2017/320052* (2013.01); *A61B 2017/320056* (2013.01); *A61B 2017/320072* (2013.01); *A61B 2017/320073* (2017.08); *A61B 2017/320074* (2017.08); *A61B 2017/320075* (2017.08); *A61B 2017/320078* (2017.08); *A61B 2017/320082* (2017.08); *A61B 2217/002* (2013.01)

(58) Field of Classification Search
CPC .......... A61B 17/320016; A61B 1/0008; A61B 17/32; A61B 1/317; A61B 1/0676; A61B 1/00094; A61B 1/00096; A61B 17/1671; A61B 1/018; A61B 1/07; A61B 5/0075; A61B 1/00165; A61B 1/00163; A61B 1/00112; A61B 1/00; A61B 2217/002; A61B 2017/320075; A61B 2017/320074; A61B 2017/320078; A61B 2017/320072; A61B 2017/320073; A61B 2017/320082; A61B 2017/320056; A61B 2017/320052
See application file for complete search history.

(56) References Cited

U.S. PATENT DOCUMENTS 4,576,145 A 3/1986 Tsuno
4,984,878 A 1/1991 Miyano
(Continued)

*Primary Examiner* — Amanda Lauritzen Moher

(57) ABSTRACT

The Vertebra Pick Device represents a new instrument to bore pilot holes in vertebra pedicles while imaging the operation with an integrated endoscope. The pilot holes are bored to provide entry points for pedicle screws that serve as anchor points for spine stabilizing rods to treat several spine conditions. The device consists of a metal body that terminates in a tapered incision tip, an endoscope that runs inside said metal body, a handle to drive the device into pedicle boney tissue and a fiber optics bundle assembly that enters the device handle and is used to connect to imaging, illumination, irrigation and suction devices to enable the endoscopic functions of the device. The fiber optics bundle assembly connects to an imaging camera that provides an electrical signal to a monitor to view the operation in real time.

27 Claims, 21 Drawing Sheets

Embodiment 1 of Vertebra Pick Device (Not to Scale)

(51) Int. Cl.
*A61B 1/018* (2006.01)
*A61B 5/00* (2006.01)

(56) References Cited

U.S. PATENT DOCUMENTS

| | | | |
|---|---|---|---|
| 5,127,393 A | | 7/1992 | McFarlin |
| 5,263,928 A | | 11/1993 | Trauthen |
| 5,928,137 A | * | 7/1999 | Green ................ A61B 1/00052 |
| | | | 600/104 |
| 7,585,274 B2 | | 9/2009 | Homma |
| 2002/0013513 A1 | * | 1/2002 | Bala ....................... A61B 1/042 |
| | | | 600/178 |
| 2002/0091390 A1 | * | 7/2002 | Michelson ......... A61B 17/1757 |
| | | | 606/86 A |
| 2003/0013936 A1 | * | 1/2003 | Jackson, III ....... A61B 17/1671 |
| | | | 600/104 |
| 2005/0080342 A1 | * | 4/2005 | Gilreath ............ A61B 1/00087 |
| | | | 600/476 |
| 2006/0161189 A1 | * | 7/2006 | Harp .................. A61B 17/1624 |
| | | | 606/171 |
| 2008/0108991 A1 | | 5/2008 | von Jako |
| 2009/0221922 A1 | * | 9/2009 | Lec ..................... A61B 5/0084 |
| | | | 600/478 |
| 2011/0098531 A1 | * | 4/2011 | To ..................... A61B 17/1671 |
| | | | 600/114 |

* cited by examiner

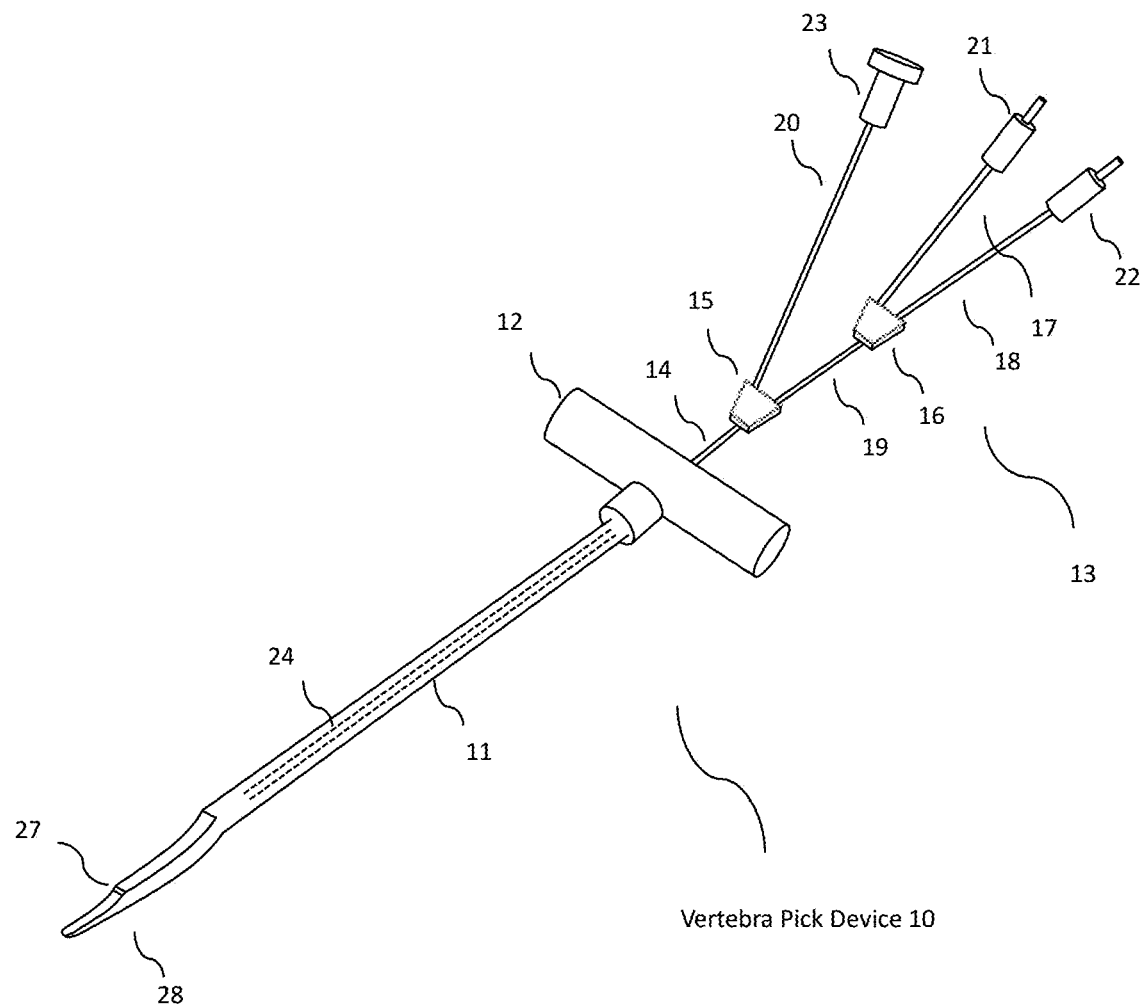
FIG.1 Embodiment 1 of Vertebra Pick Device (Not to Scale)

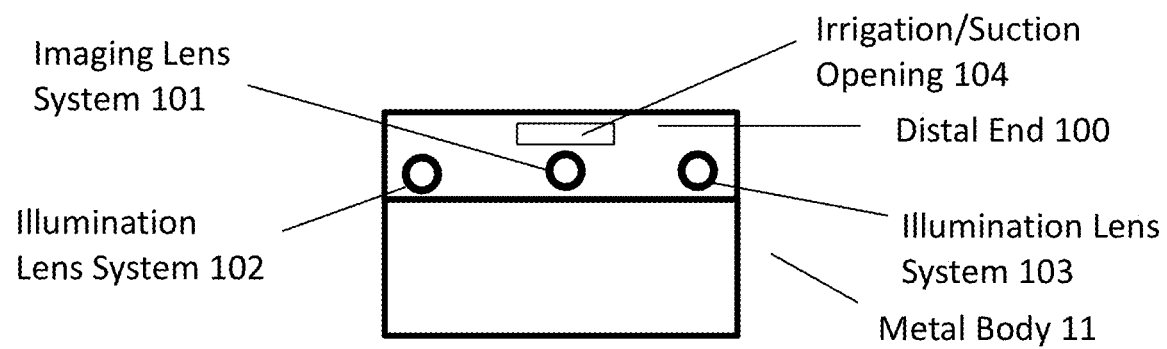
FIG. 2 Embodiment 1 of Distal End Cross Section (Not to Scale)

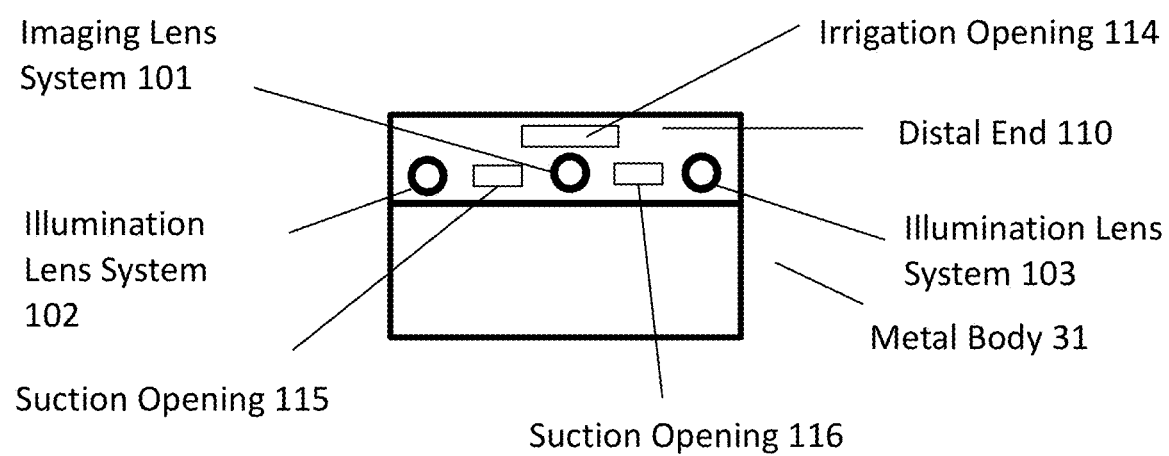
FIG.3 Embodiment 2 of Distal End Cross Section (Not to Scale)

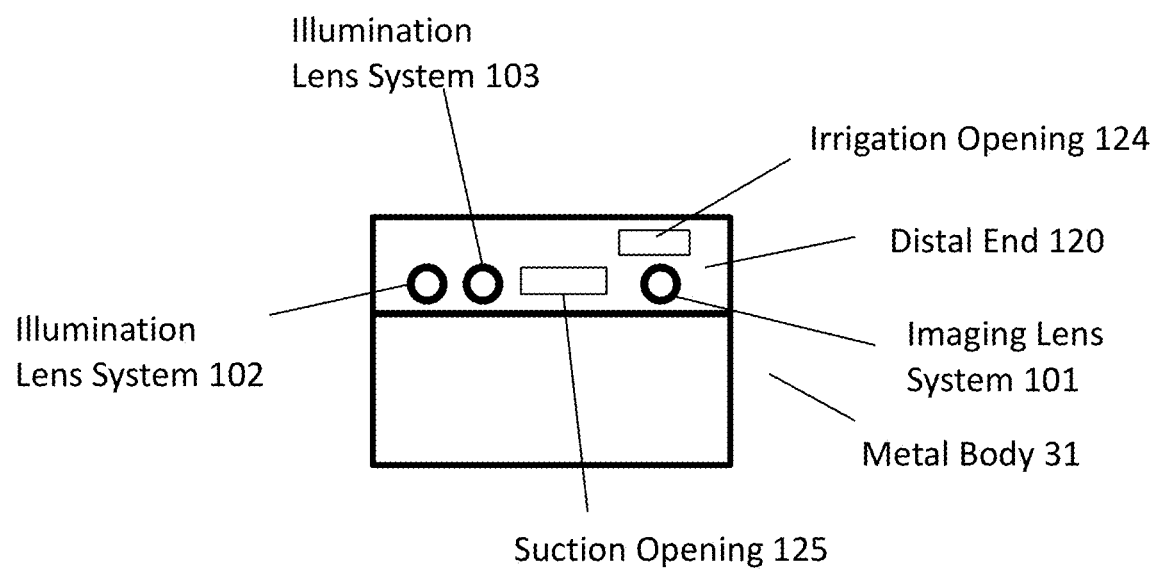
FIG. 4 Embodiment 3 of Distal End Cross Section (Not to Scale)

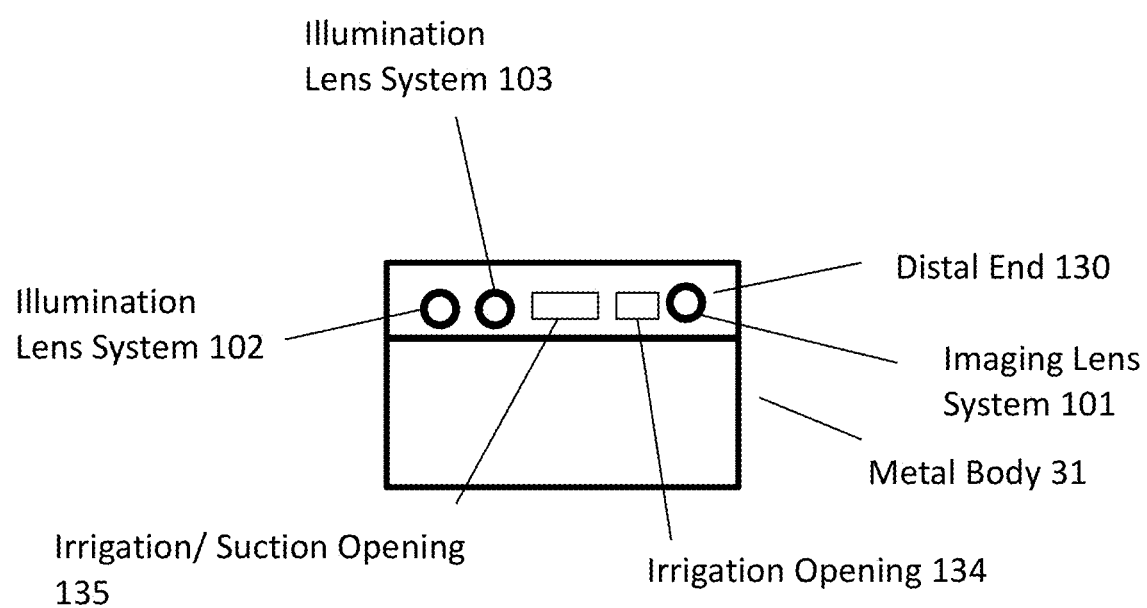
FIG. 5 Embodiment 4 of Distal End Cross Section (Not to Scale)

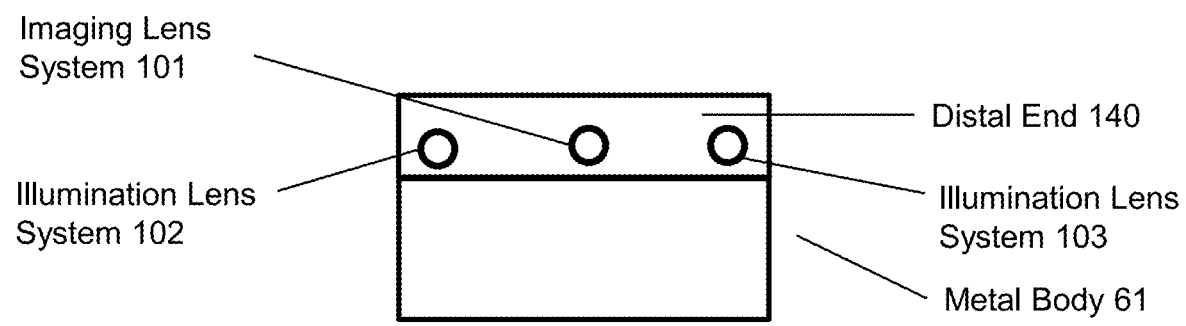
FIG. 6 Embodiment 5 of Distal End Cross Section (Not to Scale)

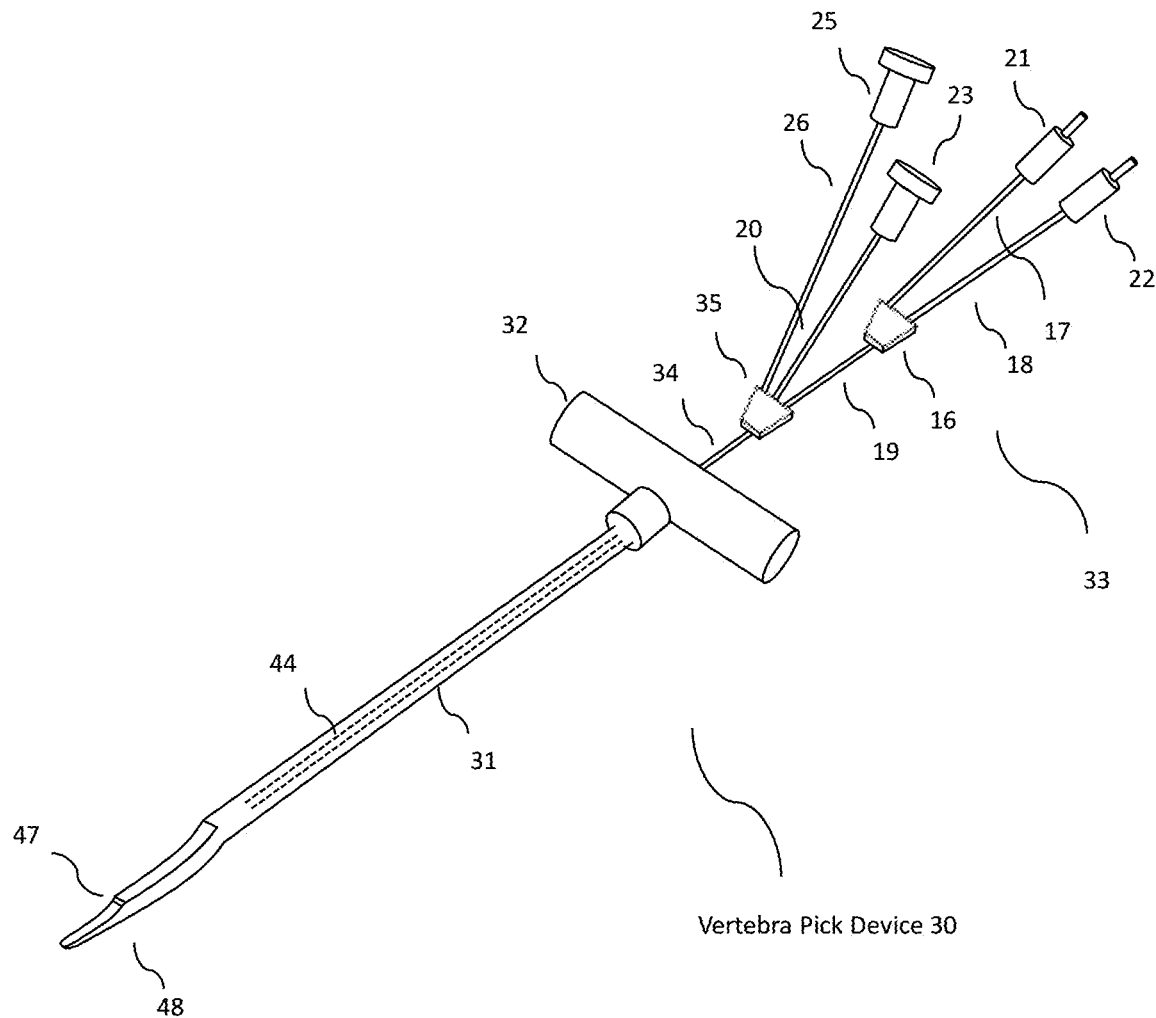
FIG. 7 Embodiment 2 of the Vertebra Pick Device (Not to Scale)

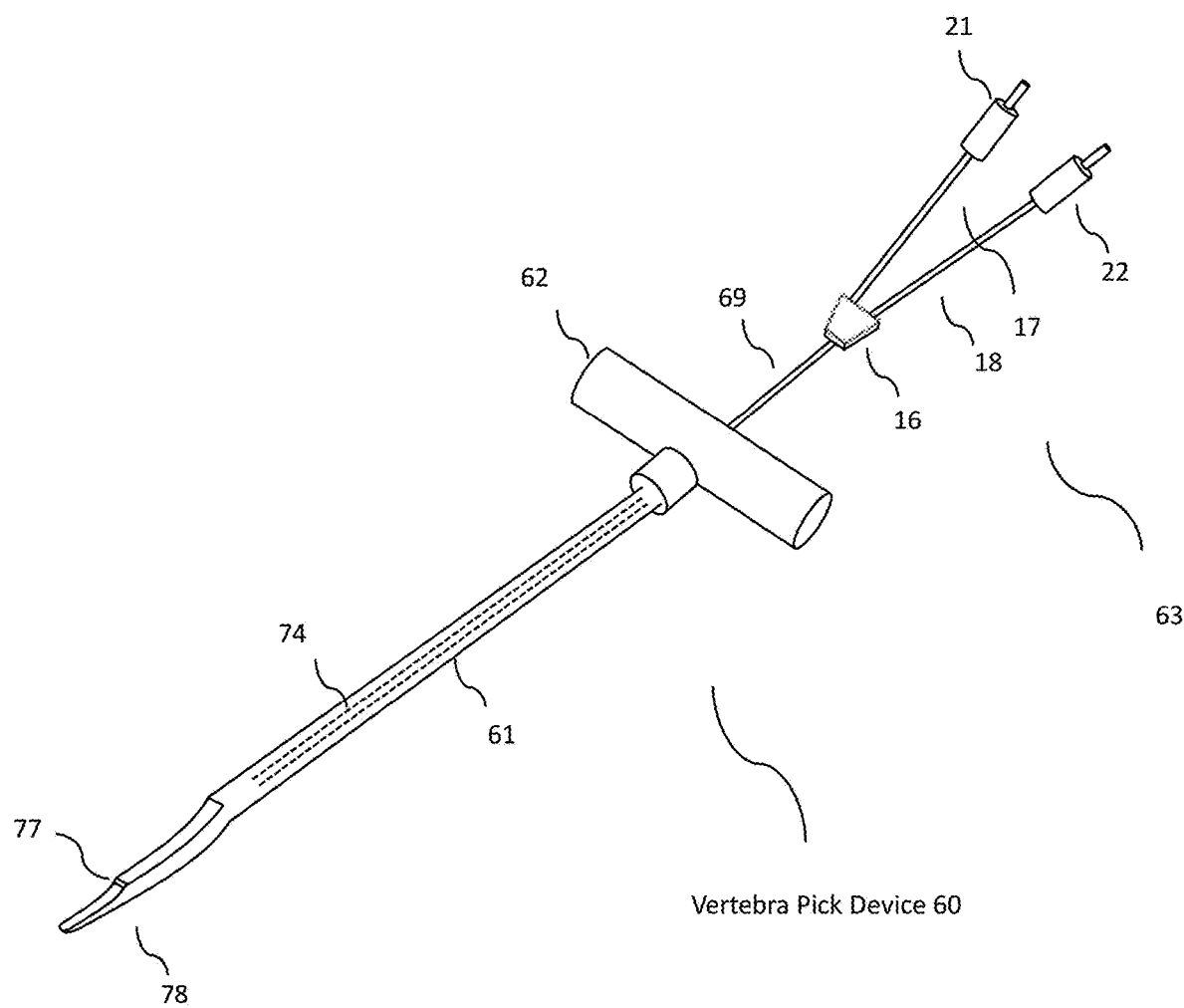
FIG. 8 Embodiment 3 of the Vertebra Pick Device (Not to Scale)

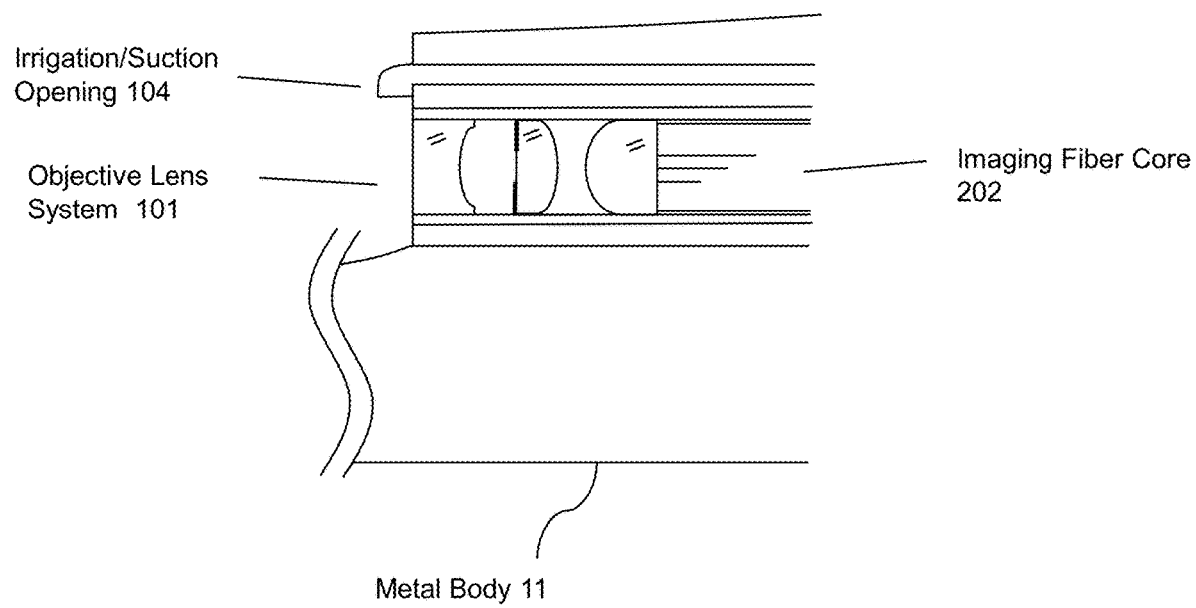
FIG. 9 Objective Lens System of Distal End Embodiment 1 (Not to Scale)

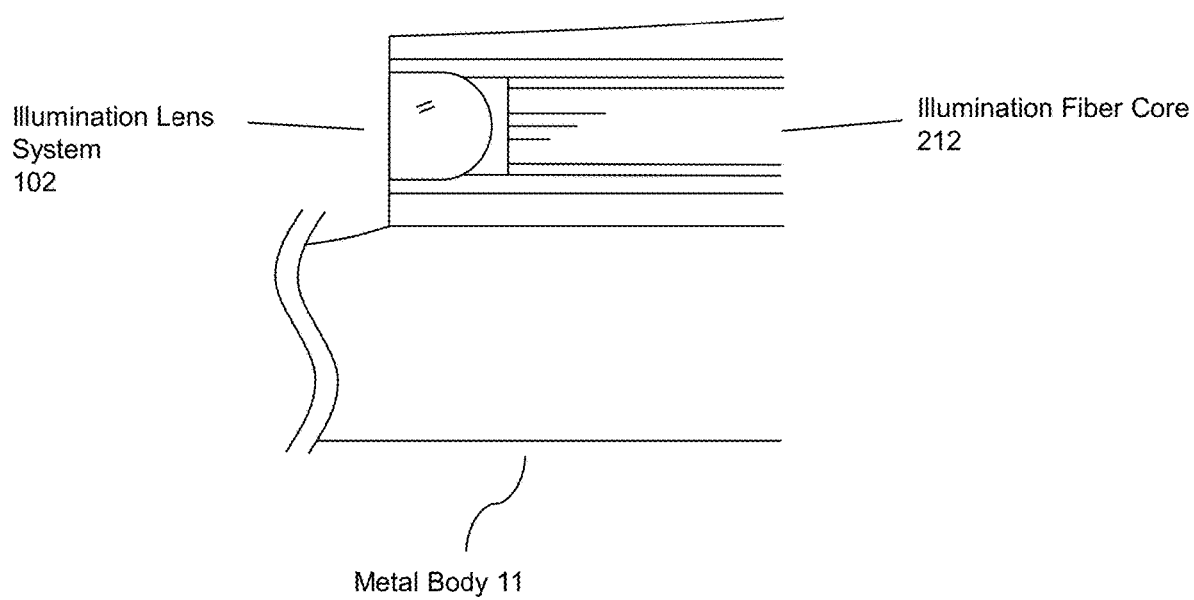
FIG. 10 Illumination Lens of Distal End Embodiment 1 (Not to Scale)

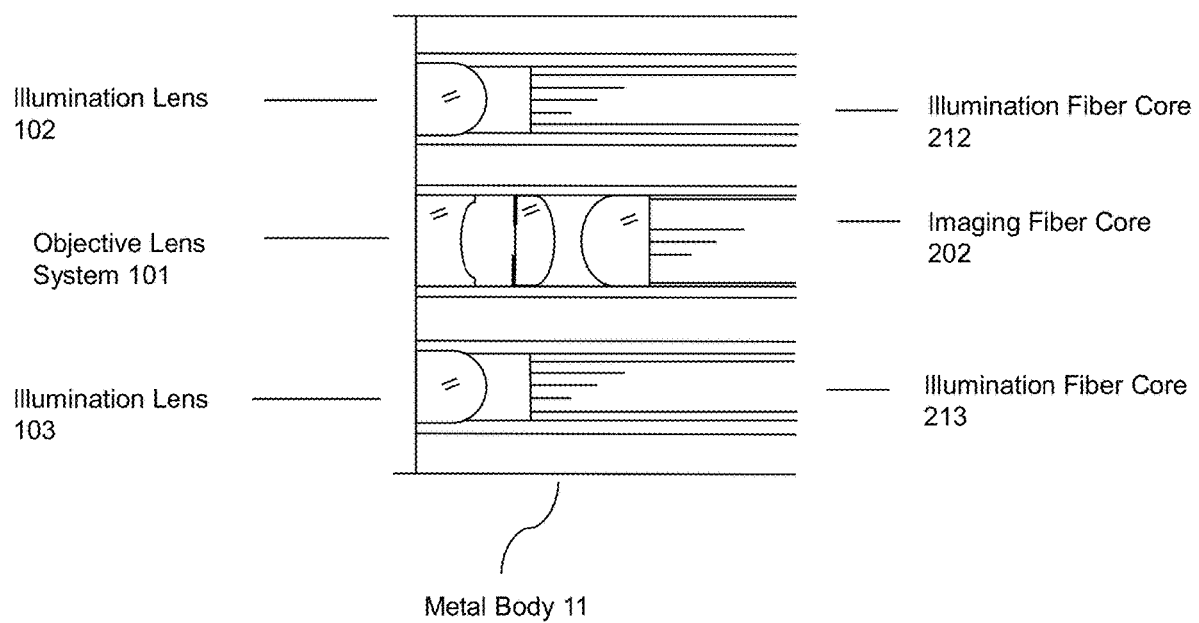
FIG. 11 Cross Section of Distal End Embodiment 1 – Horizontal Plane (Not to Scale)

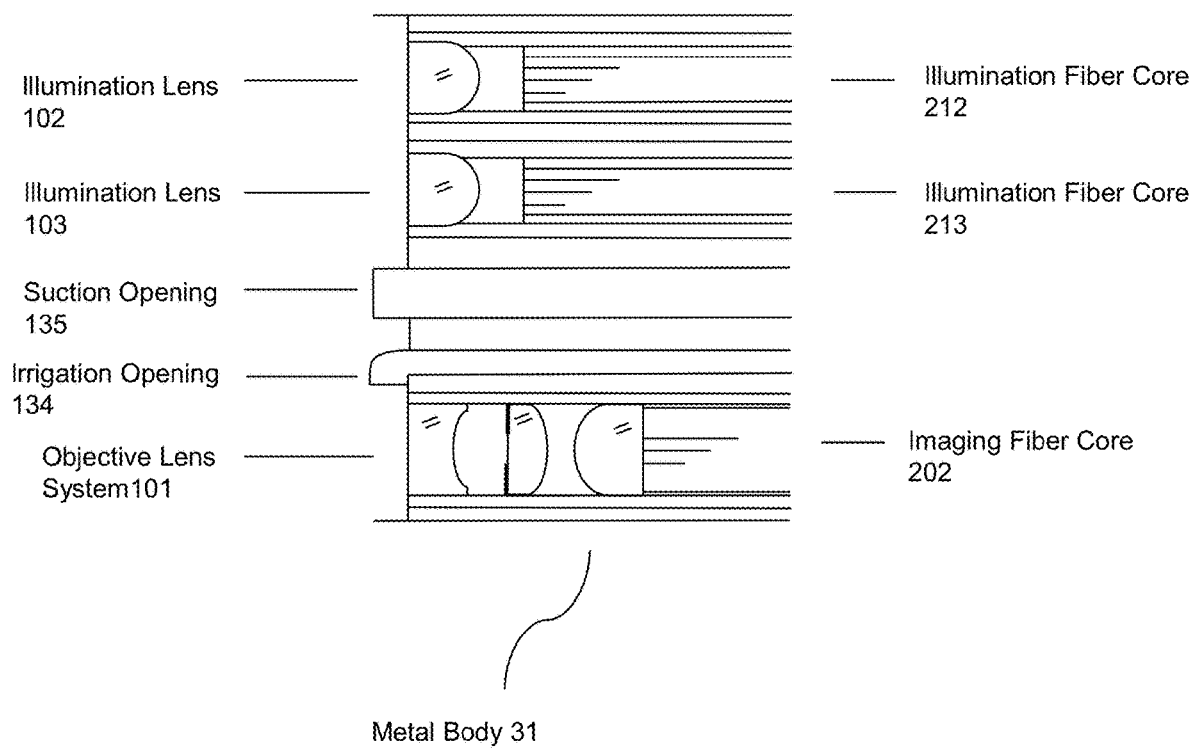
FIG. 12 Cross Section of Distal End Embodiment 4 – Horizontal Plane (Not to Scale)

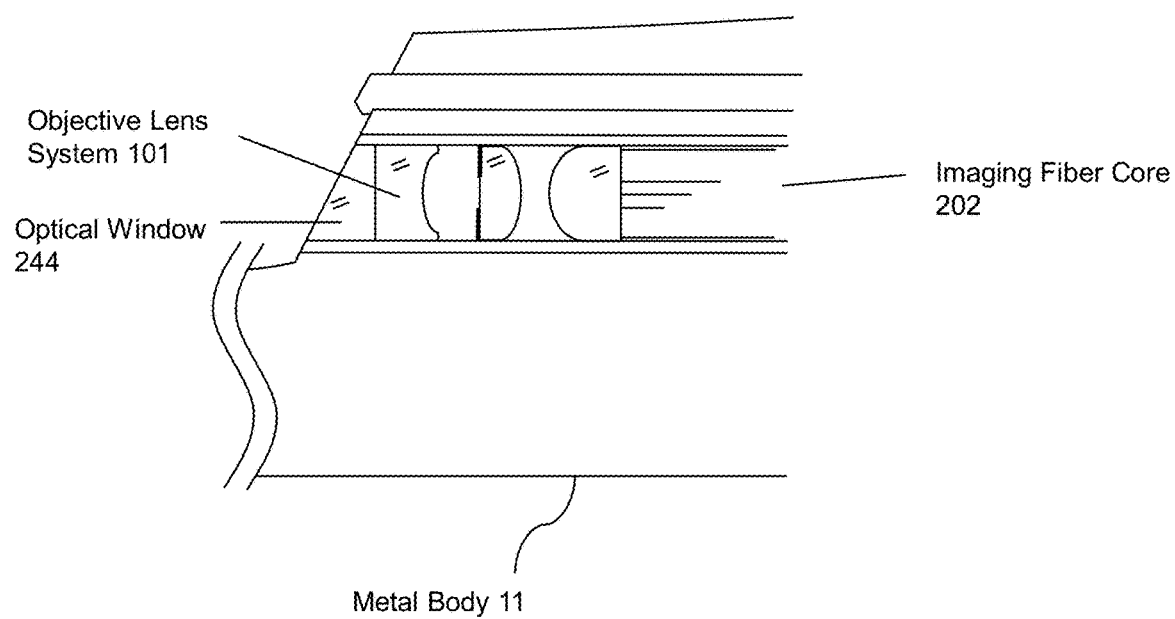
FIG. 13 Slant Design of Distal End Embodiment 1 – Objective Lens System Cross Section (Not to Scale)

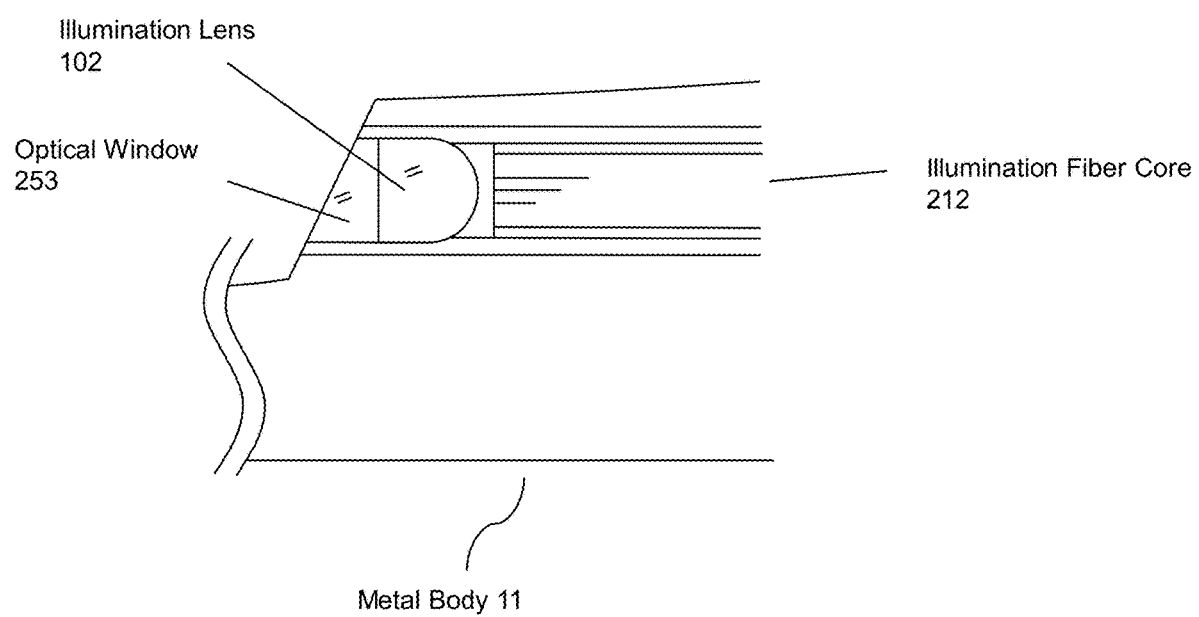
FIG. 14a Slant Design of Distal End Embodiment 1 – Illumination Lens Cross Section (Not to Scale)

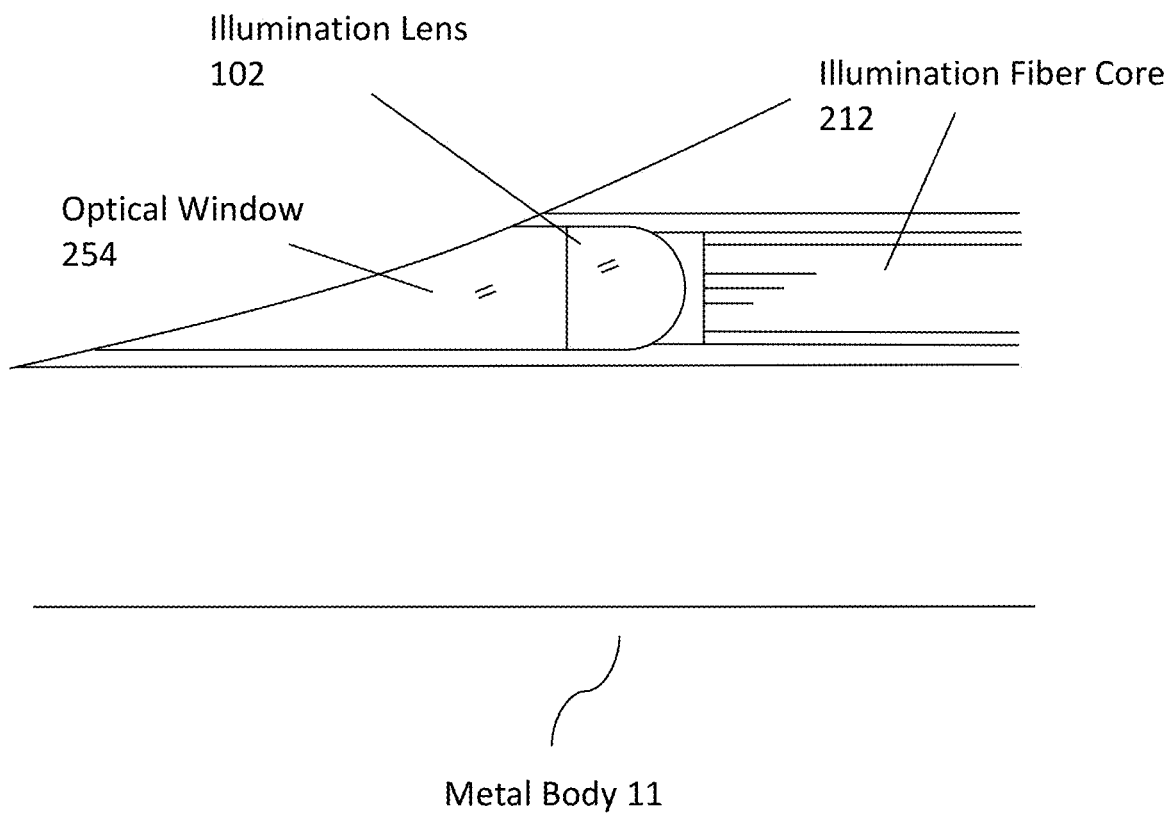
FIG. 14b Flush Design of Distal End Embodiment 1 – Illumination Lens Cross Section (Not to Scale)

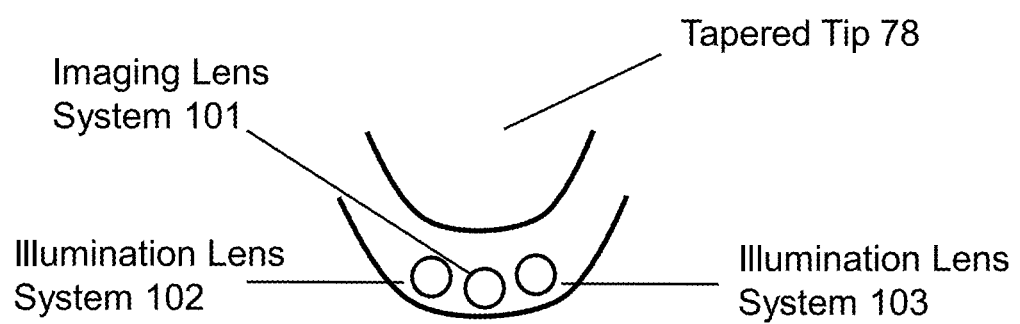
FIG. 15a Distal End with Lens Systems in the Tip Front (Not to Scale)

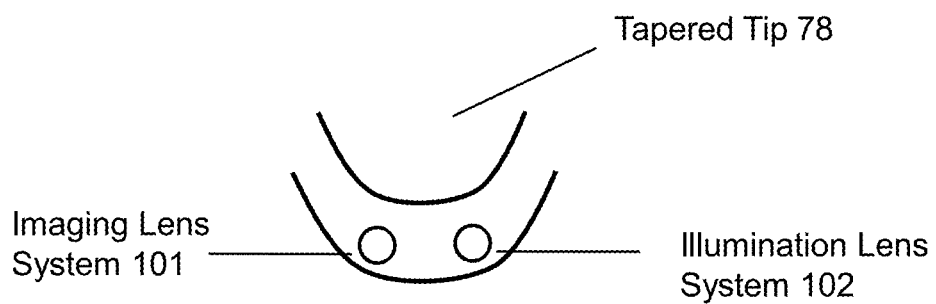
FIG. 15b Distal End with Lens Systems the Tip front (Not to Scale)

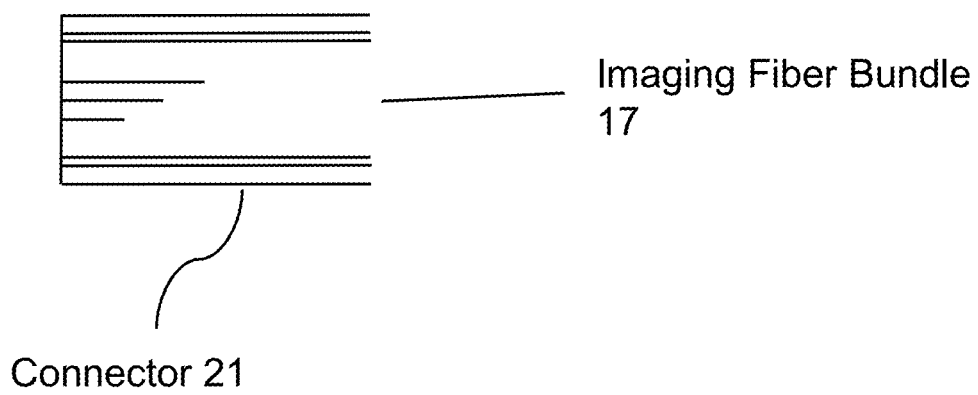
FIG. 16 Imaging Fiber Bundle Coupling Optics (Not to Scale)

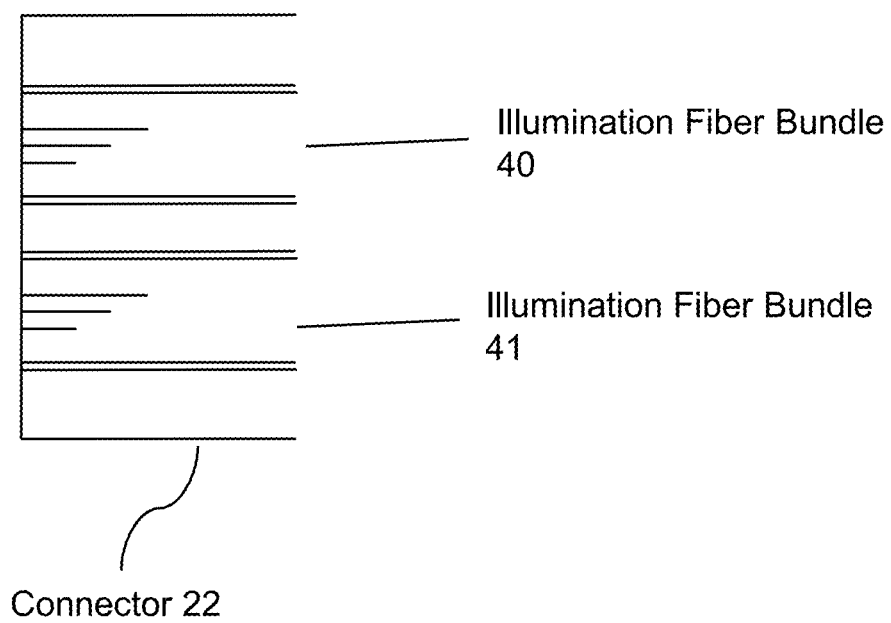
FIG.17 Illumination Fiber Bundles Coupling Optics (Not to Scale)

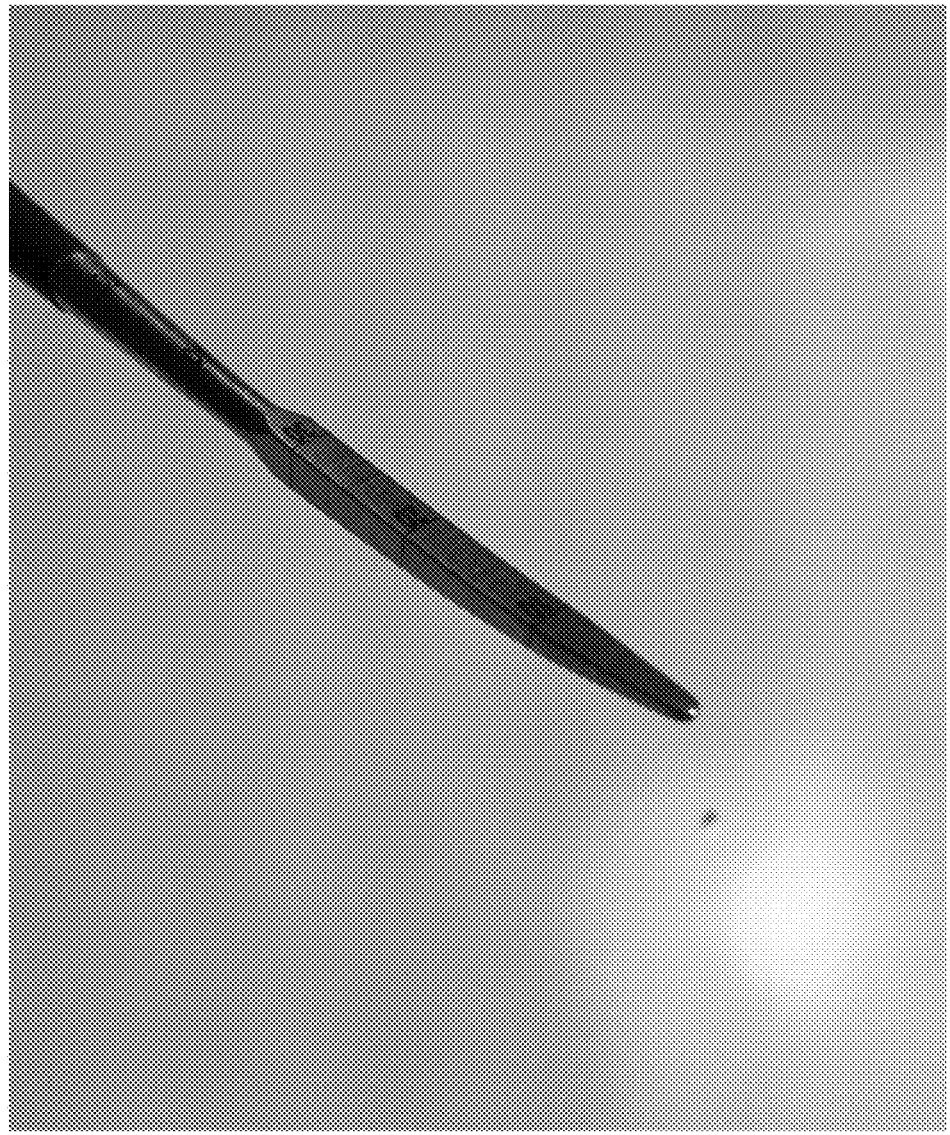
FIG.18 Sample LOB Probe Tip without Distal End

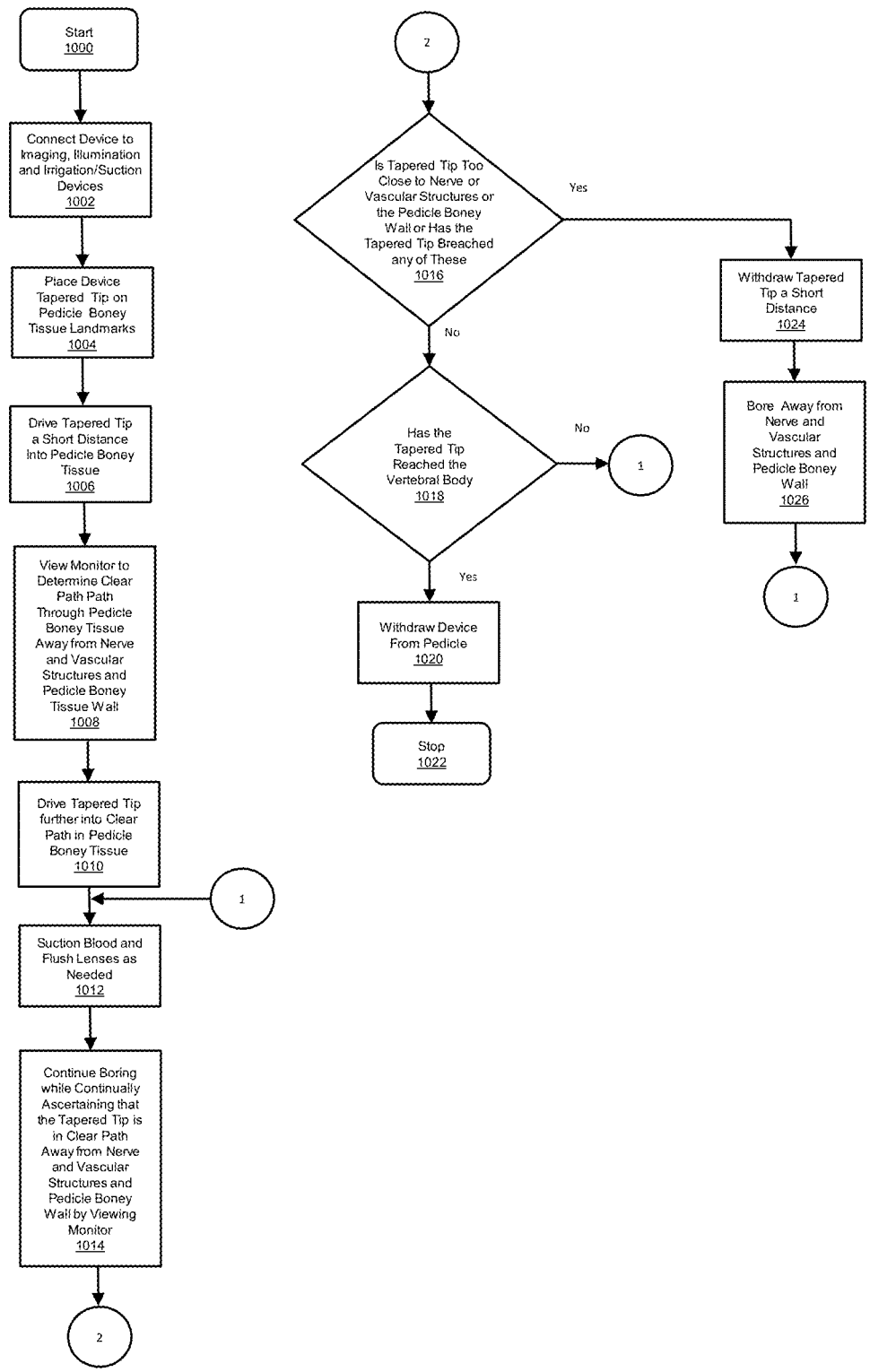
FIG. 19 Generalized Method for Creating Pilot Holes

US 10,905,452 B1

VERTEBRA PICK DEVICE

CROSS REFERENCE TO RELATED APPLICATIONS

This is a non-provisional patent application submitted as a continuation-in-part application corresponding to non-provisional patent application Ser. No. 13/731,070, Vertebra Pick Device submitted on Dec. 30, 2012.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not Applicable.

DESCRIPTION OF DRAWINGS

FIG. 1 shows embodiment 1 of the overall architecture of the device. The device provides an external interface to a camera that provides an electrical signal to a monitor to view video. It also provides interfaces to a Light Emitting Diode (LED) and to an irrigation/suction device.

FIG. 2 shows embodiment 1 of the optical system layout. The diagram is a cross section that depicts one objective lens system and two illumination lenses as well as a conduit for irrigation or air suction.

FIG. 3 shows embodiment 2 of the optical system layout. The diagram is a cross section that depicts one objective lens system and two illumination lens systems. It also shows an irrigation conduit above the objective lens system and two suction conduits, one on each side of the objective lens system.

FIG. 4 shows embodiment 3 of the optical system layout. The diagram is a cross section that depicts one objective lens system and two illumination lenses. The illumination lenses are on one side while the objective lens is on the other side and separated from them by the suction opening. The Irrigation opening is above the objective lens system.

FIG. 5 shows embodiment 4 of the optical system layout. The diagram is a cross section that depicts one objective lens system and two illumination lenses. The illumination lenses are on one side while the objective lens is on the other side. A suction and irrigation conduits are between the illumination and imaging fiber bundles, the suction opening being next to the illumination fiber bundles while the irrigation opening being next to the imaging fiber bundles.

FIG. 6 shows embodiment 5 of the optical system layout. The diagram is a cross section that depicts one objective lens system and two illumination lenses.

FIG. 7 shows embodiment 2 of the architecture of the Vertebra Pick Device. The device provides an external interface to a camera, which provides an electrical signal to a monitor to view video. It also provides interfaces to an LED, to an irrigation device and to a suction device. The irrigation and suction conduits are separate.

FIG. 8 shows embodiment 3 of the Vertebra Pick Device architecture. The device provides an external interface to a solid state imaging camera, which provides an electrical signal to a monitor to view images. It also provides an interface to an LED assembly.

FIG. 9 shows a cross section of the objective lens system of embodiment 1 of the optical system. The cross section is on a plane perpendicular to the Vertebra Pick Device body.

FIG. 10 shows a cross section of one of the illumination lenses of embodiment 1 of the optical system. The cross section is on a plane perpendicular to the Vertebra Pick Device body.

FIG. 11 shows a cross section of embodiment 1 of the optical system. The cross section is on a plane horizontal to the Vertebra Pick Device body and shows the objective lens system and the illumination lenses.

FIG. 12 shows a cross section of embodiment 4 of the optical system. The cross section is on a plane horizontal to the Vertebra Pick Device body and shows the objective lens system and the illumination lenses plus the irrigation and suction conduits.

FIG. 13 shows a cross section of the slant design of embodiment 1 of the optical system. The cross section is on a plane perpendicular to the Vertebra Pick Device through the objective lens system and irrigation conduit.

FIG. 14a shows a cross section of the slant design of embodiment 1 of the optical system. The cross section is on a plane perpendicular to the Vertebra Pick Device through one of the illumination lenses.

FIG. 14b shows a cross section of the flush design of embodiment 1 of the optical system. The cross section is on a plane perpendicular to the Vertebra Pick Device through one of the illumination lenses.

FIG. 15a shows the front of the tapered tip of the vertebra pick device with the layout of the objective lens system and the illumination lens systems.

FIG. 15b shows the front of the tapered tip of the vertebra pick device with the layout of the objective lens system and the illumination lens system.

FIG. 16 shows the coupling optics of the imaging fiber bundle. The figure shows the coupling to an imaging camera optical assembly (not shown).

FIG. 17 shows the coupling optics of the illumination fiber bundles. The figure shows the coupling to an LED optical assembly (not shown).

FIG. 18 shows a sample tapered tip of a Vertebra Pick Device without the optical system.

FIG. 19 shows a generalized flow chart of the process to create pilot holes in vertebrae.

BACKGROUND OF THE INVENTION

The invention described herein relates generally to spine surgical devices and more particularly to optically-guided spine pedicle probes for improving the imaging of the boring of pilot holes by a surgeon.

Pilot holes are created in the pedicle for subsequent insertion of pedicle screws that serve as anchor points for spine stabilization fixtures to treat several spine conditions. These pilot holes are typically created by a pedicle probe which has a sharp pointed end that is used to bore the hole through the pedicle at an appropriate angle and depth. Integrity of the pilot holes is determined by X-rays or MRI imaging or fluoroscopy but this process is not well adapted for optimal boring in the sense that corrections during the boring process are difficult to attain in real-time or the boring process is not exact.

US2008010899A1 describes a device that performs the function of an awl to perform the boring of the pilot hole, and a tap to create threads on the hole walls for the pedicle screws. The method used to perform these functions can also rely on ancillary imaging techniques, using devices that are too expensive and may not provide accurate mapping of the boring process.

The vertebra pick device described herein provides integrated real-time imaging of the boring process at selected visible or infrared wavelengths with an optical assembly, namely an endoscope. Infrared imaging particularly can see through bone tissue and image the vascular and nerve structures that surround the pedicle to determine whether the sharp tip of the device is close to them before causing any damage.

SUMMARY OF THE INVENTION

The Vertebra Pick Device represents a new way to safely place pedicle screws while imaging the operation with the aid of fiber optics technology. The operation is performed to create holes in the vertebrae to provide an entry point for screws for various spinal conditions. Currently, using a free-hand technique, fluoroscopy and/or image guidance, a probe is used to blindly create a pilot hole. The probe path is radiographically imaged to ensure that the probe follows a proper path. The probe is re-directed and the pilot hole is completed. The pilot hole is tapped, blindly, and a screw inserted. The Vertebra Pick Device provides real time imaging and continuous monitoring of the pilot hole creation into bone, allowing re-direction of the probe as necessary to avoid vital vascular and neural structures. This not only leads to safer and more accurate screw placement, but optimized screw length and diameter, as imaging, fluoroscopy in particular, can be misleading. The disposable design of the Vertebra Pick Device also ensures sharpness and optimal optics in every use. This method builds on a classic method of spinal instrumentation, and regardless of spinal deformity, allows the surgeon for safe and accurate spinal instrumentation avoiding the inherent dangers of radiation and use of very expensive guidance systems.

DETAILED DESCRIPTION OF THE INVENTION

Non-provisional patent application No. 13731070 is described herein with amendments, namely four new layouts of the fiber bundles in the Vertebra Pick Device, an additional introduction of separate suction and irrigation conduits, a design without irrigation and suction conduits, and generalized placement of the optical system in the device incision tapered tip. Furthermore, the invention described herein can be modified for operation in the infrared (IR) spectrum by appropriate changes, including changes to IR imaging cameras, IR illumination diodes and possible scaling of the optical systems. In addition, representative objective and illumination lens systems for the optical system are described. Notwithstanding, the same geometry of the device is described as well as the same fiber optics bundle assembly with the single suction/irrigation conduit.

As shown in FIG. 1, embodiment 1 of the Vertebra Pick Device 10 design consists of a metal body 11, the integrated Fiber Optics (FO) assembly 24, the endoscope, that runs inside the length of the metal body 11, a handle 12 to drive the Vertebra Pick Device and a fiber optics bundle assembly 13 that enters the handle 12. The probe terminates in a tapered tip 28 used to make incisions in vertebrae. The fiber optics assembly optical system 27 is located at a distance d1 from the probe tip which is tapered until it reaches the top of the metal body at a distance of 2.5 cm to 5 cm from the tapered tip front.

The Vertebra Pick Device allows surgeons to precisely create pilot holes in pedicle bones, which are created to place pedicle screws to anchor spine stabilizing rods. This method is unique since by choosing the proper light wavelength tissue becomes transparent allowing a surgeon to select the proper path for the boring of the pilot holes. This operation can be viewed in real-time in a video monitor such that pilot holes can be created solely in bone tissue while avoiding vital vascular and nerve structures. The device is designed to create such pilot holes in that the tip is shaped in such a way to perforate bone tissue in the same fashion as a pick. In addition, the endoscope embedded inside the device metal body provides video at the selected wavelength to monitor the operation in its entirety.

FIG. 19 describes a generalized method to create pilot holes in vertebrae using the Vertebra Pick Device. The Vertebra Pick Device is connected to imaging, illumination and irrigation/suction devices to enable its endoscopic functions at the selected visible or infrared light wavelength 1002. The tapered tip 28 is placed on the selected vertebra's pedicle at predetermined boney landmarks 1004. The tapered tip 28 is then driven a short distance into the pedicle boney tissue by manipulating the surgical device with its handle 1006 while determining in the monitor a clear path through pedicle boney tissue away from nerve or vascular structures or the pedicle boney wall 1008. Next, the tapered tip 28 is further driven into said clear path in the pedicle boney tissue 1010. Blood is suctioned as needed while the lens systems are flushed as needed in case of obstructions 1012. Boring is continued while continually ascertaining that the tapered tip 28 is in said clear path through pedicle boney tissue away from nerve and vascular structures and the pedicle boney wall by viewing the operation in the monitor 1014. A determination is made whether the tapered tip 28 is too close to nerve or vascular structures or the pedicle boney wall or whether the tapered tip has breached any of these 1016. If not, another determination is made whether tapered tip has reached the vertebral body 1018. If so, the device is withdrawn 1020 as the pilot hole has been created and the process is ended 1022. If in determination 1016 the tapered tip is too close to the nerve or vascular structures or the pedicle boney wall or if the tapered tip has breached any of these, the tapered tip 28 is withdrawn a little 1024 while continuing boring away from nerve and vascular structures and the pedicle boney wall 1026 as the process continues to process step 1012. If in determination 1018 the tapered tip has not reached the vertebral body, the process continues to process step 1012. The length of the pilot hole is determined from the markings imprinted on the vertebral pick device. Step 1012 is omitted in embodiment 3 of the Vertebra Pick Device since this embodiment lacks irrigation and suction conduits.

White or infrared light illumination from an LED source is carried by the two endoscope fiber bundles which are embedded in the channels in the Vertebra Pick Device body 11, 31, and 61 in FIGS. 1, 7 and 8, respectively. At the optical system output, these two fiber bundles illuminate the region where the Vertebra Pick Device is to make the incision in the vertebra. The other endoscope fiber bundles carries the imaging of the incision operation in the visible light spectrum. The imaging is carried to an external optical assembly and solid state imaging camera, connected to the imaging fiber bundle 17 of the fiber optics bundle assembly 13 in FIG. 1. In addition to the endoscope fiber bundles, the endoscope irrigation/suction conduit runs along the length of the Vertebra Pick Device body.

Embodiment 2 of the Vertebra Pick Device is the same as embodiment 1 except that the fiber optics bundle assembly 33 has two separate irrigation and suction conduits instead of having a single irrigation/suction conduit. Also, embodiment 2 has separate irrigation and suction conduits in the metal body 31.

Embodiment 3 of the Vertebra Pick Device, shown in FIG. 8, is the same as embodiment 1 except that the fiber optics bundle assembly 63 has no irrigation/suction conduit and the metal body 61 just has channels for one endoscope imaging fiber bundle and two endoscope illumination fiber bundles.

In embodiment 1 of the fiber optics bundle assembly 13, the Vertebra Pick Device 10 provides three connectors 21, 22 and 23. Connector 21 couples with the imaging camera optics connector (not shown) while connector 22 couples with the LED optics connector (not shown). Illumination fiber assembly 18 contains two illumination fiber bundles 40 and 41 as shown in FIG. 17. The imaging fiber bundle 17 and illumination fiber assembly 18 merge at the fiber optics merging point 16, which is a plastic molded junction from where the fiber bundles emerge into a single assembly 19. Connector 23 couples with the irrigation or suction device and is the terminating point for the irrigation/suction conduit 20, a plastic tube. Conduit 20 merges with the fiber optics assembly 19 at junction 15 from which a single integrated bundle assembly 14 emerges. The bundle assembly 14 enters the Vertebra Pick Device handle 12 where the imaging fiber bundle continues to the imaging fiber bundle of the endoscope in the Vertebra Pick Device metal body 11, each illumination fiber bundle continues to its respective illumination fiber bundle of the endoscope and the irrigation/suction conduit continues to the irrigation/suction channel of the endoscope.

In embodiment 2 of the fiber optics bundle assembly 33, shown in FIG. 7, the Vertebra Pick Device 10 provides four connectors 21, 22, 23 and 25. Connector 21 couples with the imaging camera optics connector (not shown) while connector 22 couples with the LED optics connector (not shown). Illumination fiber assembly 18 contains two illumination fiber bundles 40 and 41 as shown in FIG. 17. The imaging fiber bundle 17 and illumination fiber assembly 18 merge at the fiber optics merging point 16, which is a plastic molded junction from where the fiber bundles emerge into a single assembly 19. Connector 23 couples with the irrigation device and is the terminating point for the irrigation conduit 20, a plastic tube, while connector 25 couples with the suction device and is the terminating point for the suction conduit 26, a plastic tube. Conduits 20 and 26 merge with the fiber optics assembly 19 at junction 35 from where a single integrated bundle assembly 34 emerges. The bundle assembly 34 enters the Vertebra Pick Device handle 32 where the imaging fiber bundle continues to the imaging fiber bundle of the endoscope in the Vertebra Pick Device metal body 31, each illumination fiber bundle continues to its respective illumination fiber bundle of the endoscope, the irrigation conduit continues to the irrigation conduit of the endoscope and the suction conduit continues to the suction conduit of the endoscope.

Embodiment 3 of the fiber optics bundle assembly 63, FIG. 8, is the same as embodiment 1 of the bundle assembly except that there is no irrigation/suction conduit. As a result, the FO assembly 69 that emerges from junction 16 enters the handle 62 and the design is devoid of junction 15 and conduit 20.

The integrated FO assembly is embedded inside of the metal probe as the endoscope and contains three fiber bundles. A cross section of embodiment 1 of the optical system 100 is shown in FIG. 2. The optical system creates a small step, 27 in FIG. 1, in the tapered tip 28. The objective lens system 101 is encased in the imaging channel and is located in the middle of the probe. The illumination lenses 102 and 103 are located on both sides of the optical system. An irrigation and suction channel 104 is located on top of the objective lens system to clear blood and other debris and maintain an unobstructed field of view. This opening terminates in a protruding bend to protect it from impact as shown in FIG. 9. The same channel is used to suction excess blood, so an external device provides the switch to change between irrigation and suction modes. The optical system is forged as part of the probe metal design for which channels are created along the metal body to accommodate the fiber bundles, the optical system lenses and the irrigation and suction conduits.

Referring to the optical system design in FIG. 2, a cross section of the optical system on a plane perpendicular to the Vertebra Pick Device body 11 is shown in FIG. 9. The plane slices the middle of the optical system and shows the arrangement of the objective lens system 101 and the imaging fiber bundle 202 as well as the irrigation/suction channel 104 on top of the objective lens system. The irrigation nozzle terminates in a bend to protect the opening from impact and to direct the water flow towards the objective lens system. Although the figure shows the patented lenses described herein, other lens designs could be used.

In addition, a cross section of the optical system on a plane perpendicular to the Vertebra Pick Device body 11 is shown in FIG. 10. The plane slices one side of the optical system through the illumination lens 102, which is shown along with its respective illumination fiber bundle 212. Although the figure shows the patented lenses described herein, other lens designs could be used.

Another view of the optical system design in FIG. 2 is shown on a plane horizontal to the Vertebra Pick Device body 11 in FIG. 11. The figure shows the arrangement of the objective lens system 101 and imaging fiber bundle 202 of the endoscope as well as the illumination lenses 102/103 and their respective illumination fiber bundles 212/213 of the endoscope. Although the figure shows the patented lenses described herein, other lens designs could be used. The irrigation and suction opening is above the horizontal plane on top of the objective lens system and is not shown.

In embodiment 2 of the optical system, a cross section of the optical system 110 is shown in FIG. 3. The optical system creates a small step, 47 in FIG. 7, in the tapered tip 48. The objective lens system 101 is encased in the imaging channel and is located in the middle of the probe. Next to the objective lens system are two suction openings 115 and 116 that bifurcate from the main suction channel that runs along of the probe metal body 31. These openings terminate in a protruding bend to protect them from impact in the same manner as that of the irrigation opening. The illumination lenses 102 and 103 are located on both sides of the optical system. An irrigation channel 114 is located on top of the objective lens system to clear blood and other debris and maintain an unobstructed field of view. This opening terminates in a protruding bend to direct liquid flow and to protect it from impact. The optical system is forged as part of the probe metal design for which channels are created along the metal body to accommodate the fiber bundles, the optical system lenses and the irrigation and suction conduits.

In embodiment 3 of the optical system, a cross section of the optical system 120 is shown in FIG. 4. The optical system creates a small step, 47 in FIG. 7, in the tapered tip 48. The objective lens system 101 is encased in the imaging channel and is located on the right side. The illumination lenses 102 and 103 are located on the left side of the optical system. An irrigation channel 124 is located on top of the objective lens system to clear blood and other debris and maintain an unobstructed field of view. This opening terminates in a protruding bend to direct liquid flow and to protect it from impact in a similar manner as shown in FIG. 9. Next to the objective lens system is the suction opening 125 of the corresponding suction conduit that runs along the metal body of the probe. This opening terminates in a protruding bend to protect it from impact in the same manner as the irrigation opening. The optical system is forged as part of the probe metal design for which channels are created along the metal body to accommodate the fiber bundles, the optical system lenses and the irrigation and suction conduits, which all together comprise the endoscope.

In embodiment 4 of the optical system, a cross section of the optical system 130 is shown in FIG. 5. The optical system creates a small step, 47 in FIG. 7, in the tapered tip 48. The objective lens system 101 is encased in the imaging channel and is located on the right side of the optical system. The illumination lenses 102 and 103 are located on the left side of the optical system. An irrigation channel 134 is located next to the objective lens system to clear blood and other debris and maintain an unobstructed field of view. This opening terminates in a protruding bend that points sideways toward the objective lens system to direct liquid flow and to protect it from impact. Next to the irrigation conduit is the suction opening 135 of the corresponding suction conduit that runs along the metal body of the probe. The optical system is forged as part of the probe metal design for which channels are created along the metal body to accommodate the fiber bundles, the optical system lenses and the irrigation and suction conduits, which all together comprise the endoscope.

A cross section of embodiment 5 of the optical system 100 is shown in FIG. 6 and is the representation of embodiment 3 of the Vertebra Pick Device design and embodiment 3 of the bundle assembly. The optical system creates a small step, 77 in FIG. 8, in the tapered tip 78. The objective lens system 101 is encased in the imaging channel and is located in the middle of the probe. The illumination lenses 102 and 103 are located on both sides of the optical system. The optical system is forged as part of the probe metal design for which channels are created along the metal body to accommodate the fiber bundles, the optical system lenses and the irrigation and suction conduits, which all together comprise the endoscope.

Referring to the optical system design in FIG. 5, FIG. 12 shows a cross section of the optical system on a plane horizontal to the Vertebra Pick Device body 31. The figure shows the arrangement of the objective lens system 101 and imaging fiber bundle 202 of the endoscope as well as the illumination lenses 102/103 and their respective illumination fiber bundles 212/213 of the endoscope. Although the figure shows the patented lenses described herein, other lens designs could be used. The figure also shows the arrangement of the Irrigation opening where the nozzle bend points towards the objective lens system. In addition, the figure depicts the suction opening where the nozzle bend points down.

Embodiments 2, 3 and 4 of the optical system are different instantiations in embodiment 2 FIG. 7 of the Vertebra Pick Device in that the fiber bundles, the irrigation and suction conduits that run along the length of the metal body 31, which all together comprise the endoscope, are placed differently inside the body.

Objective and Illumination lens designs could be implemented by several of the patented designs published in the literature. Patent U.S. Pat. No. 4,984,878 FIG. 11 shows a side view of an objective lens system design. This lens system is composed of three lens elements wherein the first lens on the object side is a plano-concave negative lens with the plane surface on the object side. The second lens is a plano-convex lens having the plane surface on the object side and finally a third plano-convex lens having the plane side on the image side and contiguous to the fiber bundle of the endoscope that carries the imaging. The trade-off in this case is to miniaturize the lens diameter as much as possible while keeping a wide field of view.

A candidate illumination lens design is described in U.S. Pat. No. 7,585,274 FIG. 28 and consists of a single plano-convex lens element with the plane side on the object side. A fiber bundle located at a distance d2 from the convex side carries light from a light source and transmits it through the lens. This lens design is suitable for miniaturization while keeping a wide field of view.

In other embodiments, the optical system designs in FIGS. 2 through 5 can be modified to produce slant end designs. For example, FIG. 13 shows a side view on the plane perpendicular to the Vertebra Pick Device body 11 through the objective lens system 101, regarding the modification to the optical system design of FIG. 2 wherein the front is inclined at an angle theta. A slant optical window 244 faces the object side of the objective lens system. FIG. 14*a* also shows a side view on the plane perpendicular to the Vertebra Pick Device body 11 through one of the illumination lenses 102. A slant optical window 253 precedes the illumination lens.

In further embodiments, the optical system end designs in FIGS. 2 through 5 can be modified to produce optical systems that are flush to the tapered tip for the objective lens system and the illumination lens systems. For example, FIG. 14*b* shows a side view on the plane perpendicular to the Vertebra Pick Device body 11 through the illumination lens system 102, regarding the modification to the optical system design of FIG. 2. A flush optical window 254 precedes the illumination lens.

Other embodiments of the optical system consist of placing the objective lens system 101 and the illumination lens systems 102 and 103 in front of the tapered tip 78 for Embodiment 3 of the device as shown in FIG. 15*a* and FIG. 15*b*. In FIG. 15*a* as seen from the front, the objective lens system 101 is on the left of the center of the tapered tip 78 while the illumination lens system 102 is on the left side of the tapered tip 78 and the illumination lens system 103 is on the right side of the tapered tip 78. In FIG. 15*b* as seen from the front, the objective lens system 101 is on the left side of the tapered tip 78 while there is only one illumination lens system 102 on the right side of the tapered tip 78. In all cases, the lens systems are preceded by optical windows that are flush to the shape of the tip. An irrigation and suction conduit may be added on top of objective lens system if these designs are used with Embodiment 1 of the Vertebra Pick Device.

The imaging lens system is such that objects can be focused from 1 mm to ~10 cm. Also, the illuminating lens system provides uniform illumination for the imaging field of view. On the other end, the fiber optics bundles provide the lens systems that interface with the imaging camera optical assembly and the LED optical assembly. This is shown in FIG. 1.

The number of fibers in the imaging fiber bundle of the endoscope is on the order of 10,000 fibers, a trade-off number that provides excellent resolution of the object image. The imaging fiber bundle of the endoscope continues to the imaging fiber bundle in the integrated assembly 14 or 34 of the fiber optics bundle assembly external to the Vertebra Pick Device handle. The camera provides an electrical signal to a monitor to provide video to medical personnel.

The LED assembly illuminates the incision by transmitting light through the illumination fiber bundles of the fiber optics bundle assembly and the illumination fiber bundles of the endoscope. The illumination fiber bundles of the endoscope and the illumination fiber bundles of the fiber optics bundle assembly consist of a plurality of fibers, on the order of 300 to 1000 glass fibers each. The illumination fiber bundles of the endoscope and the illumination fiber bundles of the fiber optics bundle assembly provide the means to carry light from the LEDs with enough intensity and low attenuation such that the emitted light at the output of the illumination lens allows the objective lens system to discern objects with clarity. The placement of the illumination fiber bundles of the endoscope with respect to optical system lens is such that essentially all light can be output at the optical system. Another option is to implement the illumination fiber bundles of the endoscope with plastic fibers with a diameter of around 500 microns in which case each illumination fiber bundles would consist of a single plastic fiber.

The imaging fiber bundle proximal end of the fiber optics bundle assembly 17 terminates on a plane perpendicular to the axis of the fiber bundle as shown in FIG. 16. When the proximal end connector 21 connects to the camera, the imaging fiber bundle proximal lens remains fixed at distance d3 such that, in conjunction with the camera lens system, the image is placed on the solid state imaging plane. Light is emitted from the imaging fiber bundle as a function of the numerical aperture of the fiber bundle with the camera lens system performing all the focusing of the image signal onto the imaging plane.

The proximal end of each illumination fiber bundle of the fiber optics bundle assembly terminates flush on a plane perpendicular to the fiber longitudinal axis as shown in FIG. 17. The illumination fiber bundle connector 22 mates with the LED connector such that each fiber bundle is placed at a fixed distance from the LED, which consists of a single fixture coupled to both illumination fiber bundles. The LED lens systems implements all the focusing of its light into the two fiber bundles such that the fibers capture the light as a function of their numerical aperture. The illumination fiber bundles are coaxially placed next to each other and thereby the LED illuminates both of them on an area comprised of the terminating circle areas. The LED lens system radiates light into the illumination fiber bundles so that a large fraction of the light is coupled into the fibers.

The other external interface is to an irrigation device and to a suction device. The interfaces to these devices are implemented in embodiments 1 and 2 of the Vertebra Pick Device in FIGS. 1 and 7.

FIG. 18 shows the tip of a Vertebra Pick Device with a stainless steel fabrication. The Vertebra Pick Device tip described herein is similar in design except that the optical system is placed near the front of the tapered tip, producing a small step in the integrated design, or in front of the tapered tip.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

The invention claimed is:

1. A method for creating and imaging pilot holes in pedicle bone of vertebrae to accommodate insertion of pedicle screws by using an endoscopic surgical device and operating the endoscopic surgical device at selected visible wavelengths for imaging of the pilot hole inner walls or diffused imaging of the same or at selected infrared wavelengths for imaging through the pilot hole walls to determine the location of the nerve and vascular structures located on the outer surface of the pedicle bone of vertebrae and avoid rupturing said nerve and vascular structures while viewing the surgical operation on a monitor, the method for creating and imaging pilot holes with said endoscopic surgical device, during a surgical operation, comprising the steps of: connecting said endoscopic surgical device to an imaging device, an illumination device and irrigation and suction devices to enable the endoscopic functions of said endoscopic surgical device; placing said tapered tip on the selected pedicle bone of vertebrae at predetermined boney landmarks; driving the tapered tip of said endoscopic surgical device a short distance into the tissue of the pedicle bone of vertebrae by manipulating said endoscopic surgical device with its handle; determining in the monitor a clear path through the tissue of the pedicle bone of vertebrae away from nerve and vascular structures and the boney wall of the pedicle bone of vertebrae; driving said tapered tip further into said clear path through the tissue of the pedicle bone of vertebrae; suctioning blood as needed throughout the surgical operation and flushing the optical system of the endoscope as needed to clear obstructions throughout the surgical operation; continuing boring while continually ascertaining that said tapered tip is in said clear path through the tissue of the pedicle bone of vertebrae away from nerve and vascular structures and the boney wall of the pedicle bone of vertebrae by viewing the operation in the monitor; withdrawing said tapered tip a short distance if said tapered tip gets too close to nerve or vascular structures or the boney wall of the pedicle bone of vertebrae or if said tapered tip has breached the nerve or vascular structures or the boney wall of the pedicle bone of vertebrae by viewing the operation in the monitor; continuing boring in a path away from nerve and vascular structures and the boney wall of the pedicle bone of vertebrae once said tapered tip has been withdrawn a short distance if said tapered tip has gotten too close to nerve or vascular structures or the boney wall of the pedicle bone of vertebrae or if said tapered tip has breached the nerve or vascular structures or the boney wall of the pedicle bone of vertebrae; withdrawing said tapered tip from the pedicle bone of vertebrae if the vertebral body has been reached by viewing the operation in the monitor as the pilot hole has been created;

providing said endoscopic device with:
a tapered tip constructed of a rigid, stiff and curved metal structure configured to perform boring of the pilot hole to accommodate placement of the pedicle screws;
an elongated metal body having a distal end and a proximal end and whose distal end is formed contiguously to said tapered tip back;
an endoscope terminated in an optical system and integrated inside said elongated metal body through an internal channel that runs parallel along said elongated metal body, wherein said optical system is placed at a predetermined distance from said tapered tip front;

a handle placed in the proximal end of said elongated metal body adapted to drive said endoscopic surgical device into the pedicle bone of vertebrae;

a fiber optics bundle assembly;

wherein the tapered tip has a predetermined width at its back that gradually decreases to a pointy and sharp front;

wherein the tapered tip has a predetermined height at its back and gradually curves to said pointy and sharp front;

wherein said endoscope is comprised of one imaging system comprised of an imaging fiber bundle terminated in an objective lens system, two illumination systems each one comprised of an illumination fiber bundle terminated in an illumination lens system, and an irrigation and suction conduit;

wherein the optical system is placed is placed at a predetermined distance from the front of the tapered tip;

wherein said fiber optics bundle assembly is comprised of an imaging fiber bundle encased in a first plastic housing, two illumination fiber bundles encased in a second plastic housing, and an irrigation and suction conduit wherein the imaging fiber bundle merges with the two illumination fiber bundles at a first plastic-molded junction to emerge in a fiber optics assembly that encases individually the imaging fiber bundle and the two illumination fiber bundles in a third plastic housing and wherein the irrigation and suction conduits further merges with the fiber optics assembly at a second plastic-molded junction to emerge in an integrated assembly that encases individually the imaging fiber bundle, the two illumination fiber bundles, and the irrigation and suction conduits in a fourth plastic housing and enters the handle;

wherein said imaging fiber bundle of said fiber optics bundle assembly transitions to said endoscope imaging system as the single imaging fiber bundle to provide imaging functions by connecting at its proximal end to an imaging device through one imaging connector, wherein said two illumination fiber bundles of said fiber optics bundle assembly further transition individually to said two illumination systems of said endoscope as the two illumination fiber bundles to provide illumination functions by connecting at their proximal end to an illumination device through one illumination connector, and wherein said irrigation and suction conduit of said fiber optics bundle assembly further transitions to said endoscope irrigation and suction conduit as the single irrigation and suction conduit to provide irrigation and suction functions by connecting at its proximal end to irrigation and suction devices through one irrigation and suction connector;

wherein said optical system terminates flush on top of said tapered tip and wherein said optical system is located at a predetermined distance from said tapered tip front wherein said objective lens system is preceded by a first flush optical window, wherein one of the two illumination lens systems is preceded by a second flush optical window, and wherein the second illumination system is preceded by a third flush optical window;

wherein said optical system is a rectangular structure with said objective lens system in the center with respect to the view from the front of the tapered tip, one illumination lens system on left side of the objective lens system, and another illumination lens system on the right side of the objective lens system, said irrigation conduit on top of the objective lens system, and said suction conduit is bifurcated with one opening between the objective lens system and the illumination lens system on the left side of the objective lens system and the other opening between the objective lens system and the illumination lens system on the right side of the objective lens system.

2. An endoscopic surgical device configured to create pilot holes in pedicle bone of vertebrae for subsequent insertion of pedicle screws by imaging such of operation of the pedicle bone of vertebrae at selected visible or infrared light wavelengths to avoid rupturing of the outer nerve and vascular structures of the pedicle bone of vertebrae, the endoscopic surgical device comprising: a tapered tip constructed of a rigid, stiff and curved metal structure configured to perform boring of the pilot hole to accommodate placement of the pedicle screws; an elongated metal body having a distal end and a proximal end and whose distal end is formed contiguously to said tapered tip back; an endoscope terminated in an optical system and integrated inside said elongated metal body through an internal channel that runs along said elongated metal body, wherein said optical system is placed at a predetermined distance from said tapered tip front; a handle placed in the proximal end of said elongated metal body adapted to drive said endoscopic surgical device into the pedicle bone of vertebrae; and a fiber optics bundle assembly; wherein the tapered tip has a predetermined width at its back that gradually decreases to a pointy and sharp front; and wherein the tapered tip has a predetermined height at its back and gradually curves to said pointy and sharp front.

3. The endoscopic surgical device in claim 2 wherein the endoscope is comprised of an imaging system comprised of an imaging fiber bundle terminated in an objective lens system, two illumination systems each one comprised of an illumination fiber bundle terminated in an illumination lens system, and an irrigation and suction conduit.

4. The endoscopic surgical device in claim 3 wherein said fiber optics bundle assembly is comprised of an imaging fiber bundle encased in a first plastic housing, two illumination fiber bundles encased in a second plastic housing, an irrigation conduit and suction conduit wherein the imaging fiber bundle merges with the two illumination fiber bundles at a first plastic-molded junction to emerge in a fiber optics assembly that encases individually the imaging fiber bundle and the two illumination fiber bundles in a third plastic housing and wherein the irrigation and suction conduit further merge with the fiber optics assembly at a second plastic-molded junction to emerge in an integrated assembly that encases individually the imaging fiber bundle, the two illumination fiber bundles, and the irrigation and suction conduit in a fourth plastic housing and enters the handle; wherein said imaging fiber bundle of said fiber optics bundle assembly transitions to said endoscope imaging system as the single imaging fiber bundle to provide imaging functions by connecting at its proximal end to an imaging device through one imaging connector, wherein said two illumination fiber bundles of said fiber optics bundle assembly further transition individually to said two illumination fiber bundles of said endoscope as the two illumination fiber bundles to provide illumination functions by connecting at their proximal end to an illumination device through one illumination connector, and wherein said irrigation and suction conduit of said fiber optics bundle assembly further transitions to said endoscope irrigation and suction conduit as the single irrigation and suction conduit to provide irrigation and suction functions by connecting at its proximal end to irrigation and suction devices through one irrigation and suction connector.

5. The endoscopic surgical device in claim 3 wherein said optical system end consists of a vertical step on top of said tapered tip and wherein said optical system end is located at a predetermined distance from said tapered tip front.

6. The endoscopic surgical device in claim 3 wherein said optical system consists of a slanted step on top of said tapered tip and wherein said optical system is located at a predetermined distance from said tapered tip front wherein the objective lens system is preceded by a first slanted optical window, wherein one of the two illumination lens systems is preceded by a second slanted optical window, and wherein the second illumination system is preceded by a third slanted optical window.

7. The endoscopic surgical device in claim 3 wherein said optical system terminates flush to said tapered tip and wherein said optical system is located at a predetermined distance from said tapered tip front wherein the objective lens system is preceded by a flush optical window and wherein each illumination lens system is preceded by a flush optical window.

8. The endoscopic surgical device in claim 3 wherein said optical system is a rectangular structure with the objective lens system in the center of said optical system with respect to the view from the front of the tapered tip, one of the two illumination lens systems on the left side of the objective lens system, and the second illumination lens system on the right side of the objective lens system, and the irrigation and suction conduit on top of the objective lens system; wherein the optical system is placed at a predetermined distance from the front of said tapered tip.

9. The endoscopic surgical device in claim 1 wherein the endoscope is comprised of an imaging system comprised of an imaging fiber bundle terminated in an objective lens system, two illumination systems each one comprised of an illumination fiber bundle terminated in an illumination lens system, an irrigation conduit, and a suction conduit.

10. The endoscopic surgical device in claim 9 wherein said fiber optics bundle assembly is comprised of an imaging fiber bundle encased in a first plastic housing, two illumination fiber bundles encased in a second plastic housing, an irrigation conduit and a suction conduit wherein the imaging fiber bundle merges with the two illumination fiber bundles at a first plastic-molded junction to emerge in a fiber optics assembly that encases individually the imaging fiber bundle and the two illumination fiber bundles in a third plastic housing and wherein the irrigation and suction conduits further merge with the fiber optics assembly at a second plastic-molded junction to emerge in an integrated assembly that encases individually the imaging fiber bundle, the two illumination fiber bundles, and the irrigation and suction conduits in a fourth plastic housing and enters the handle; wherein said imaging fiber bundle of said fiber optics bundle assembly transitions to said endoscope imaging system as the single imaging fiber bundle to provide imaging functions by connecting at its proximal end to an imaging device through one imaging connector, wherein said two illumination fiber bundles of said fiber optics bundle assembly further transition individually to said two illumination systems of said endoscope as the two illumination fiber bundles to provide illumination functions by connecting at their proximal end to an illumination device through one illumination connector, wherein said irrigation conduit of said fiber optics bundle assembly further transitions to said endoscope irrigation conduit as the single irrigation conduit to provide irrigation functions by connecting at its proximal end to an irrigation device through one irrigation connector, and wherein said suction conduit of said fiber optics bundle assembly further transitions to said endoscope suction conduit as the single suction conduit of said fiber optics bundle assembly to provide suction functions by connecting at its proximal end to a suction device through one suction connector.

11. The endoscopic surgical device in claim 9 wherein said optical system consists of a vertical step on top of said tapered tip and wherein said optical system is located at a predetermined distance from said tapered tip front.

12. The endoscopic surgical device in claim 9 wherein said optical system consists of a slanted step on top of said tapered tip and wherein said optical system is located at a predetermined distance from said tapered tip front wherein the objective lens system is preceded by a first slanted optical window, wherein one of the two illumination lens systems is preceded by a second slanted optical window, and wherein the second illumination lens system is preceded by a third slanted optical window.

13. The endoscopic surgical device in claim 9 wherein said optical system terminates flush on top of said tapered tip and wherein said optical system is located at a predetermined distance from said tapered tip front wherein the objective lens system is preceded by a first flush optical window, wherein one of the two illumination lens systems is preceded by a second flush optical window, and wherein the second illumination lens system is preceded by a third flush optical window.

14. The endoscopic surgical device in claim 9 wherein the optical system is a rectangular structure with the objective lens system in the center of said optical system with respect to the view from the front of the tapered tip, one of the two illumination lens systems on the left side of the objective lens system, and the second illumination lens system on the right side of the objective lens system, the irrigation conduit on top of the objective lens system and the suction conduit is bifurcated with one opening between the objective lens system and the illumination lens system on the left side of the objective lens system and the other opening between the objective lens system and the illumination lens system on the right side of the objective lens system; wherein the optical system is placed at a predetermined distance from the front of the tapered tip.

15. The endoscopic surgical device in claim 9 wherein the optical system is a rectangular structure with the objective lens system in the center of said optical system with respect to the view from the front of the tapered tip, the two illumination lens systems on the left side of said optical system, the irrigation conduit on top of the objective lens system and the suction conduit between the objective lens system and the two illumination lens systems; wherein the optical system is placed at a predetermined distance from the front of the tapered tip.

16. The endoscopic surgical device in claim 9 wherein the optical system is a structure with the objective lens system in the center of said optical system with respect to the view from the front of the tapered tip, the two illumination lens systems on the left side of said optical system, the irrigation conduit between the left side of the objective lens system and the right side of the illumination lens systems and the suction conduit between the left side of the irrigation conduit and the right side of the illumination lens systems; wherein the optical system is placed at a predetermined distance from the front of the tapered tip.

17. An endoscopic surgical device configured to create pilot holes in pedicle bone of vertebrae for subsequent insertion of pedicle screws by imaging such operation of the pedicle bone vertebrae at selected visible or infrared light wavelengths to avoid rupturing of the outer nerve and vascular structures of the pedicle bone of vertebrae, the endoscopic surgical device comprising: a tapered tip constructed of a rigid, stiff and curved metal structure configured to perform boring of the pilot hole to accommodate placement of the pedicle screws; an elongated metal body having a distal end and a proximal end and whose distal end is formed contiguously to said tapered tip back; an endoscope terminated in an optical system and integrated inside said elongated metal body through an internal channel that runs along said elongated metal body, wherein said optical system is placed at a predetermined distance from said tapered tip front, wherein said optical system is alternately placed in the front of said tapered tip; a handle placed in the proximal end of said elongated metal body adapted to drive said endoscopic surgical device into the pedicle bone of vertebrae; and a fiber optics bundle assembly; wherein the tapered tip has a predetermined width at its back that gradually decreases to a pointy and sharp front; and wherein the tapered tip has a predetermined height at its back and gradually curves to said pointy and sharp front.

18. The endoscopic surgical device in claim 17 wherein the endoscope is comprised of an imaging system comprised of an imaging fiber bundle terminated in an objective lens system and two illumination systems each one comprised of an illumination fiber bundle terminated in an illumination lens system.

19. The endoscopic surgical device in claim 18 wherein said fiber optics bundle assembly is comprised of an imaging fiber bundle encased in a first plastic housing, two illumination fiber bundles encased in a second plastic housing wherein the imaging fiber bundle merges with the two illumination fiber bundles at a plastic-molded junction to emerge in a fiber optics assembly that encases individually the imaging fiber bundle and the two illumination fiber bundles in a third plastic housing and enters the handle; wherein said imaging fiber bundle of said fiber optics bundle assembly transitions to said endoscope imaging system as the single imaging fiber bundle to provide imaging functions by connecting at its proximal end to an imaging device through one imaging connector, and wherein said two illumination fiber bundles of said fiber optics bundle assembly further transition individually to said endoscope illumination systems as the two illumination fiber bundles to provide illumination functions by connecting at their proximal end to an illumination device through one illumination connector.

20. The endoscopic surgical device in claim 18 wherein said optical system consists of a vertical step on top of said tapered tip and wherein said optical system is located at a predetermined distance from said tapered tip front.

21. The endoscopic surgical device in claim 18 wherein said optical system consists of a slanted step on top of said tapered tip and wherein said optical system is located at a predetermined distance from said tapered tip front wherein the objective lens system is preceded by a first slanted optical window, wherein one of the two illumination lens systems is preceded by a second slanted optical window, and wherein the second illumination system is preceded by a third slanted optical window.

22. The endoscopic surgical device in claim 18 wherein said optical system terminates flush to said tapered tip and wherein said optical system is located at a predetermined distance from said tapered tip front wherein the objective lens system is preceded by a first flush optical window, wherein one of the two illumination lens systems is preceded by a second flush optical window and wherein the second illumination lens system is preceded by a third flush optical window.

23. The endoscopic surgical device in claim 18 wherein said optical system is a flush structure which is part of the front of said tapered tip, wherein said objective lens system of said optical system is preceded by a first flush optical window and wherein said objective lens system of said optical system is located on the left side of said tapered tip front as viewed from the front of said tapered tip, wherein one of the two illumination lens systems is preceded by a second flush optical window and is located on the left side of said objective lens system as viewed from the front of said tapered tip, and wherein the second illumination lens system is preceded by a third flush optical window and is located on the right side of said tapered tip as viewed from the front of said tapered tip.

24. The endoscopic surgical device in claim 18 wherein the optical system is a rectangular structure with the objective lens system in the center of said optical system with respect to the view from the front of the tapered tip, one of the two illumination lens systems on the left side of the objective lens system, and the second illumination lens system on the right side of the objective lens system.

25. The endoscopic surgical device in claim 17 wherein the endoscope is comprised of one imaging system terminated in an objective lens system and one illumination system terminated in an illumination lens system.

26. The endoscopic surgical device in claim 25 wherein said fiber optics bundle assembly is comprised of an imaging fiber bundle encased in a first plastic housing, two illumination fiber bundles encased in a second plastic housing wherein the imaging fiber bundle merges with the two illumination fiber bundles at a plastic-molded junction to emerge in a fiber optics assembly that encases individually the imaging fiber bundle and the two illumination fiber bundles in a third plastic housing and enters the handle; wherein said imaging fiber bundle of said fiber optics bundle assembly bundle transitions to said endoscope imaging system as the single imaging fiber bundle to provide imaging functions by connecting at its proximal end to an imaging device through one imaging connector, and wherein said illumination fiber bundle of said fiber optics bundle assembly further transitions to said endoscope illumination system as the single illumination fiber bundle to provide illumination functions by connecting at its proximal end to an illumination device through one illumination connector.

27. The endoscopic surgical device in claim 25 wherein said optical system is a flush structure which is part of the front of said tapered tip, wherein said objective lens system of said optical system is preceded by a first flush optical window and is located on the left side of said tapered tip front as viewed from the front of said tapered tip and wherein said illumination lens system is preceded by a second flush optical window and is located on the right side of said tapered tip as viewed from the front of said tapered tip.

* * * * *